United States Patent [19]

Lehmann

[11] Patent Number: 4,870,018
[45] Date of Patent: Sep. 26, 1989

[54] PROCESS AND APPARATUS FOR GASSING LIQUIDS

[75] Inventor: Jürgen Lehmann, Braunschweig, Fed. Rep. of Germany

[73] Assignee: Gesellschaft für Biotechnologische Forschung mbH (GBF), Braunschweig, Fed. Rep. of Germany

[21] Appl. No.: 855,624
[22] PCT Filed: Aug. 2, 1985
[86] PCT No.: PCT/EP85/00387
§ 371 Date: Mar. 17, 1986
§ 102(e) Date: Mar. 17, 1986

[30] Foreign Application Priority Data

Aug. 3, 1984 [DE] Fed. Rep. of Germany ....... 3428758
Aug. 22, 1984 [DE] Fed. Rep. of Germany ....... 3430924

[51] Int. Cl.$^4$ ............................................. C12N 5/00
[52] U.S. Cl. .................. 435/240.1; 435/240.25; 435/286; 435/315; 210/500.23
[58] Field of Search .......... 435/240.1, 240.24, 240.25, 435/240.46, 284, 286, 307, 313, 315; 604/4, 5, 6; 210/216, 321.67, 354, 356, 500.23

[56] References Cited

U.S. PATENT DOCUMENTS

| | | | |
|---|---|---|---|
| 3,821,108 | 6/1974 | Manjikian | 210/321.67 |
| 3,856,475 | 12/1974 | Marx | 435/284 |
| 4,075,100 | 2/1978 | Furuta et al. | 210/500.23 |
| 4,208,289 | 6/1980 | Bray | 210/321.67 |
| 4,405,688 | 9/1983 | Lowery et al. | 210/500.23 |

FOREIGN PATENT DOCUMENTS 2201903 5/1974 France .
2393535 1/1979 France .
1480406 7/1977 United Kingdom .

OTHER PUBLICATIONS

U.K. Patent Application No. GB 2059436A, 4/1981.
PCT Application No. WO85/02195, May 23, 1985, Wergeland et al.
U.K. Application No. GB 2093730, Sep. 9, 1985, Akzo, N. V.

Primary Examiner—Noah P. Kamen
Attorney, Agent, or Firm—Kane, Dalsimer, Sullivan, Kurucz, Levy, Eisele and Richard

[57] ABSTRACT

In a process and an apparatus for the bubble-free gassing of liquids, especially of culture media for propagating tissue cultures, in which process and apparatus a gas exchange occurs across an immersed membrane sheet, to achieve simple, effective and as uniform as possible a distribution of the gas introduction and gas desorption without mechanical damage to the liquid constituents, a tubular membrane cage formed by hollow membrane filaments is suspended flexibly in the medium to be gassed and moved in a circular oscillating movement without true rotation. The gassing rate is controlled by altering the angular oscillating movement frequency and/or the radius of the circular path, or alternatively by altering the gas concentration and/or the pressure of the gas flowing into the membrane cage.

15 Claims, 2 Drawing Sheets

PROCESS AND APPARATUS FOR GASSING LIQUIDS

BACKGROUND OF THE INVENTION

1. Field of the Invention

The invention relates to a process and to an apparatus for the bubble-free gassing of liquids, especially of culture media especially for propagating tissue cultures.

2. Brief Description of the Prior Art

The purpose of gassing liquids is to introduce and to desorb gases. Especially when multiplying animal cells in culture media, adequate supply of oxygen and adequate removal of carbon dioxide presents a problem if cell numbers of more than $10^6$ cells per ml of culture medium are to be achieved. Since with so-called surface gassing only a small volume of liquid can be gassed, there has been a change to so-called submersed gassing. Although the required gasification rates with air or pure oxygen can be achieved in this process, undesirable foam formation occurs at the surface of the medium. Frequently cells and also microcarriers float in this foam, and this results in a reduction in the efficiency of the culture.

To solve this problem a method has become known in which gas exchange occurs across an immersed membrane sheet. In this process, the gassing is carried out with closed or open-pored membranes that are arranged in the liquid which is agitated by a stirrer. It is to be seen as a disadvantage in this process that the movement of the liquid is in many cases possible only under certain conditions and at a very low number of revolutions since the tissue cultures are extremely sensitive to shearing forces.

The problem underlying the invention is to provide a process and an apparatus, of the type mentioned at the beginning, for the bubble-free gassing of liquids, especially of culture media for propagating tissue cultures, which process and apparatus allows as uniform as possible a distribution of gas introduction and gas desorption in a simple and effective manner without mechanical damage to the constituents of the liquid medium, like cells.

SUMMARY OF THE INVENTION

The invention comprises a process for the bubble-free gassing of liquids, especially of culture media especially for propagating tissue cultures, with a gas exchange across an immersed membrane sheet, characterised in that a hollow cylindrical membrane cage formed by porous hollow membrane filaments is suspended flexibly in the medium to be gassed, and a translatory movement is imparted to the membrane cage.

DETAILED DESCRIPTION OF THE PREFERRED EMBODIMENTS OF THE INVENTION

Figure 1:
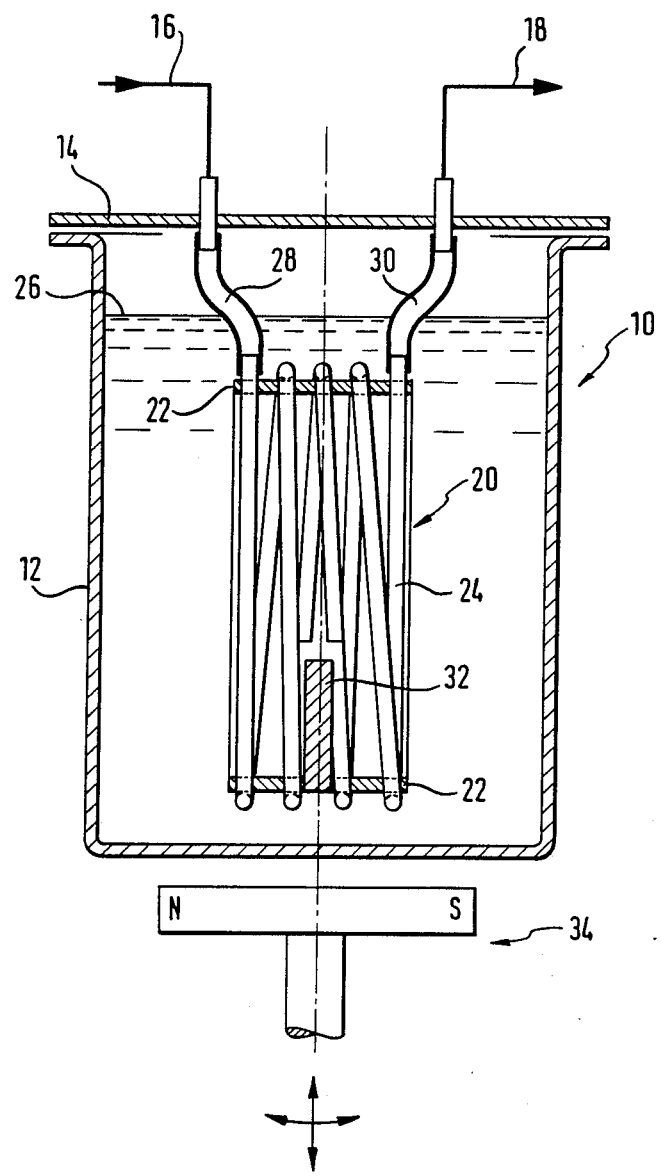
FIG. 1 is a cross-sectional side elevation of embodiment apparatus of the invention.
Figure 2:
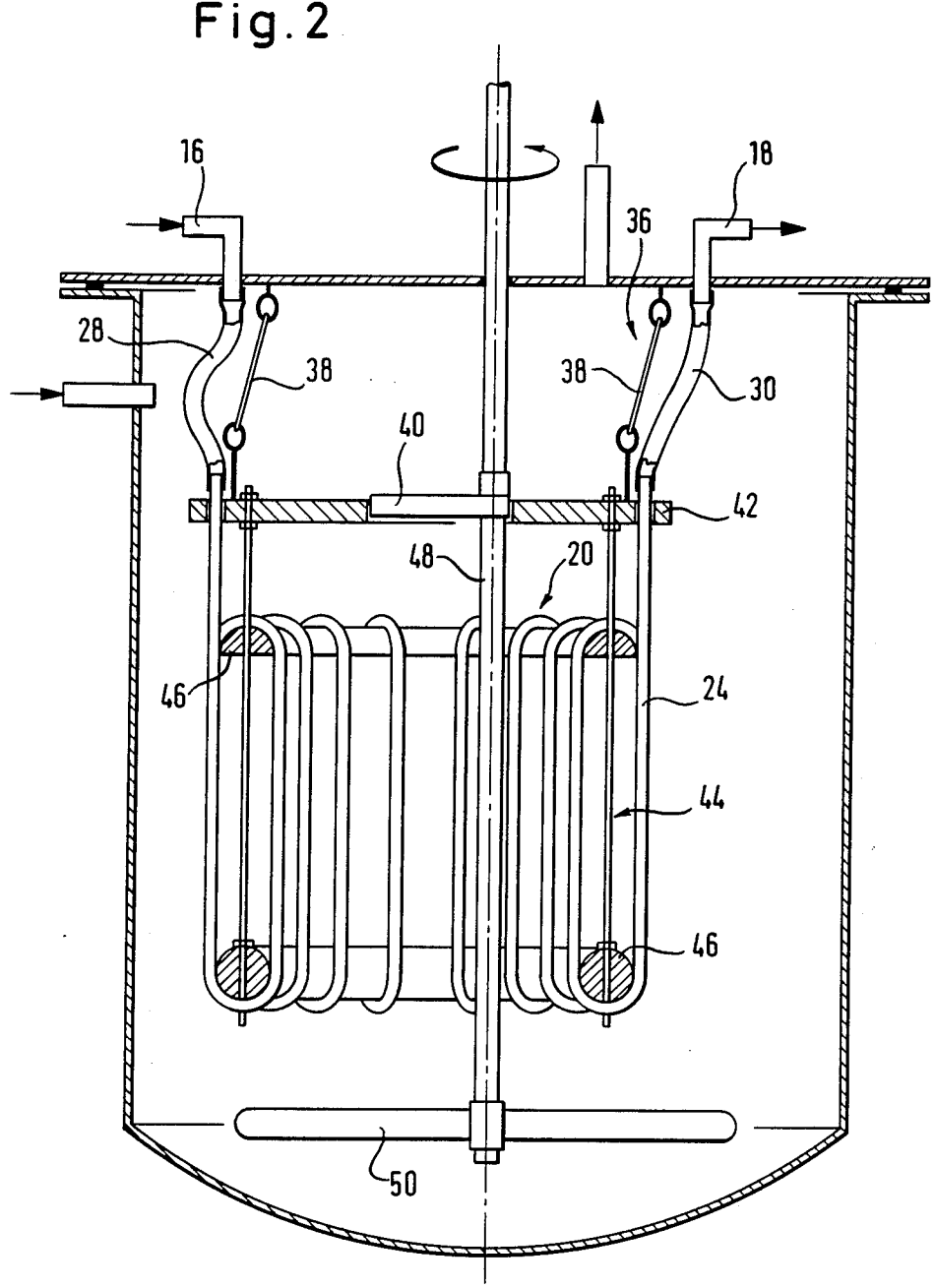
FIG. 2 is a cross-sectional side elevation of another embodiment apparatus of the invention.

By means of the process and apparatus in accordance with the invention, a uniform movement of liquid at all areas of the membrane or of the membrane cage is guaranteed, accompanied by a high boundary surface renewal rate owing to the movement of the membrane cage. Both the introduction of gas and the desorption of gas are quasi-homogeneously distributed over the entire volume of liquid without additional mixing devices being necessary. The supply and removal of gas can be carried out in an advantageous manner without having to move seals, by way of a simple coupling using flexible tubes, the tubes simultaneously being used to suspend the membrane cage. The configuration of the tubular-shaped membrane cage can, in an advantageous manner, easily be matched to the particular conditions in cell cultures, for example slime or cell agglomerate formation. This can be effected without difficulty and in an advantageous manner, for example by altering the number and the diameter of the hollow membrane filaments.

In an advantageous further development of the invention, to facilitate imparting the movement, the membrane cage can be moved without auto- or self-rotation.

The translatory movement of the membrane cage, which is preferably provided without true rotation of the membrane cage, can be initiated, for example, by way of the membrane cage suspension system. It is advantageous in this case for the membrane cage to have a magnetic core to which the movement of pendulum and/or circular movement of pendulum and/or rotary swinging movement is imparted by a magnet arrangement provided outside the medium to be gassed. The magnet arrangement can itself be moved, or can cause corresponding force-induced motion.

Especially in the case of larger amounts of liquid it is alternatively advantageous if a membrane cage, enlarged according to scale, is suspended by articulated members and is moved by means of an eccentric operating in the region of the axis of symmetry of the membrane cage. In this case, the eccentric can preferably engage into a guide plate fastened to the membrane cage, and it is especially advantageous if the axis of symmetry of the guide plate coincides with that of the membrane cage and if the guide plate is secured by means of a tension ring support to at least one slotted tension ring that, with the hollow membrane filaments, forms the membrane cage.

The gassing rate can preferably be controlled by altering the angular oscillating frequency and/or the radius of the circular path, or alternatively by altering the gas concentration and/or the pressure of the gas flowing into the membrane cage.

Further details, features and advantages of the invention are disclosed in the following part of the description in which the invention is illustrated in detail by way of two schematically represented examples of an apparatus according to the invention and by way of examples of experiments.

An apparatus (10) according to the invention, shown diagrammatically in the drawing 1, comprises a non-magnetic vessel 12, on which there is arranged a lid 14 which can optionally be fastened and sealed in a manner not shown. A gas inlet line 16 and a gas outlet line 18 are passed through the lid 14.

There is arranged in the vessel 12 a membrane cage 20 which has a membrane carrier 22 in the shape of a hollow cylinder on which hollow membrane filaments 24 are helically wound. The membrane cage 20 is completely immersed in a body of liquid 26 in the vessel 12 and is flexibly mounted at its upper end by resilient tubes 28 and 30. The tube 28 is connected to the gas inlet line 16 and to one end of the wound hollow membrane filament 24, whilst the tube 30 joins the other end of the wound hollow membrane filament 24 to the gas outlet line 18.

In the lower region of the membrane cage 20 there is attached to the membrane carrier 22, in non-rotatable manner, a magnetic core 32 which can be acted on by a magnet arrangement 34 located outside the vessel 12.

In order to impart an oscillating movement to the membrane cage 20, by way of the magnetic core 32, the magnet arrangement 34 can be moved back and forth in a linear movement by way of a device that is not shown. This linear movement is effected in such a direction that the membrane cage 20 oscillates about a straight line passing through the points of suspension.

In the lower region of the membrane cage 20 there is attached to the membrane carrier 22, in non-rotatable manner, a magnetic core 32 which can be acted on by a magnet arrangement 34 located outside the vessel 12.

In order to impart a circular oscillating movement to the membrane cage 20, by way of the magnetic core 32, the magnet arrangement 34 can be rotated by way of a device that is not shown. With this circular oscillating movement, the membrane moves on a circular path without true rotation about its axis of symmetry.

Alternatively, it is also possible to initiate a linear movement at a particular angle to the axis of symmetry of the membrane cage in order to superimpose on the linear movement of pendulum of the membrane cage, as a result of the resilience of the tubes 28 and 30, an additional component of movement which can result in an elliptical or a circular oscillating movement.

It is furthermore also possible to provide, instead of the correspondingly moved magnet arrangement 34, a stationary electromagnet arrangement, the desired movement of pendulum or circular movement of pendulum of the membrane cage being achieved by corresponding disposition and actuation of the electromagnets.

The gassing rate can be controlled by altering the circular oscillating frequency and/or the radius of the circular path. In the case of the embodiment shown, a corresponding alteration of the circular path radius can be achieved in a simple manner by altering the distance between the gas inlet line 16 and the gas outlet line 18 in the lid 14. For example, by reducing the said distance, the deflection of the membrane cage from the rest position (i.e. that position in which there is no movement imparted to the membrane cage 20 and the latter remains suspended motionless in the container 12) is correspondingly reduced.

The embodiment shown in the drawing 1 is designed especially for smaller amounts of liquid. For the bubble-free gassing of amounts of liquid of the order of 30 liters or more, the suspension by way of resilient tubes 16, 18 for the supply and removal of gas is, according to the drawing 2, advantageously taken over by a suitable suspension system 36 using flexible or pivotable articulated members 38 and the membrane cage 24, made on a larger scale, is moved with the aid of an eccentric 40. The articulated members 38 can consist, for example, of two or more tension wires of equal length which, spaced from one another, are each pivotally mounted on the lid 14 and are hinged to a guide plate 42 surrounding the eccentric 40, and of which the axis of symmetry coincides with that of the membrane cage 24. This guide plate 42 can be secured by means of a tension ring support 44 to slotted tension rings 46 which, together with the hollow membrane filament or filaments 24, form the correspondingly enlarged membrane cage. To impart a circular motion of pendulum to the membrane cage 20, there may be provided a drive shaft 48 in engagement with vessel 12 and, by way of an adjustable eccentric 40, also in engagement on or in the guide plate 42. The drive shaft 48 preferably enters through the lid 14 or the base of the vessel 12 in the region of the axis of symmetry of the vessel. If the drive shaft 48 is introduced through the lid 14 of the vessel 12, the guide plate 42 is advantageously arranged above the membrane cage 20, and the shaft 48 can be extended through the hollow cylindrical membrane cage 20 and into the lower half of the container 12, and the lower end of the drive shaft 48 can be provided with a stirrer 50. This stirrer 50 can effect a slow movement of the liquid during the first growing stage of a culture in the so-called initial cultivation phase with a low level of liquid and pure aeration over the surface.

The afore-described apparatus is also suitable as an additional system for conventional fermenters and represents an ideal supplement for existing systems.

To investigate the efficiency of the apparatus shown diagrammatically in the drawing 1, a membrane cage 20 was produced on which there had been wound a hollow membrane filament 24 made of Accurel® type PX 190/1/2/8366 with a pore volume of 75% and a pore size of 0.3 μm. The length of the hollow membrane filament 24 was 121 cm, the outer membrane surface area 98.7 cm$^2$, and the hollow membrane filament was gassed internally with pure oxygen at a superatmospheric pressure of 30 mm water column. An advantageous membrane material is especially microporous polypropylene, for example Accurel®.

The membrane cage was immersed in 1.3 l of distilled water and moved at a deflection of 2.5 cm around the centre, with 60 circular oscillations per minutes, by a rotatably mounted magnet arranged beneath the vessel.

Measurements with this apparatus showed that at a temperature of 25° C. an oxygen transfer rate OTR of 56 mg $O_2/(l.h)$ could be achieved without the appearance of oxygen bubbles from the membrane surface. This corresponds to a specific oxygen flow $Q_Oof$ 0.57 mg $O_2/(cm^2 \cdot h)$. In the case of the unmoved surface, using the same apparatus an oxygen flow $Q_{O2}$ of 0.22 mg $O_2/(cm_2 \cdot h)$ was measured.

The described apparatus is suitable, for example, for the culturing of fibroblasts, for example human diploid foreskin cells (FS-4), which have a specific oxygen requirement $q_{O2}$ of 0.05 mmol $O_2/(10^9$ cells$\cdot$h) or 1.6 mg $O_2/(10^9$ cells$\cdot$h). It was calculated that with this apparatus 3.5 $10^{10}$ cells/l could be supplied.

The following is another Example of the use of the process and apparatus: A cell culture with primary human leucocytes with a cell count n of 4.5 $10^9$ cells/l and an initial specific oxygen requirement $q_{O2}$ of 4.3 mg $O_2/(10^9$ cells$\cdot$h) was treated at 37° C. in a culture medium RPMI 1640 including some process-conditioning additives, using 60 circular oscillations per minute and an oxygen superatmospheric pressure of 30 mm water column. As oxygen-transfer rate (OTR) of 38 mg $O_2/l \cdot h$ with bubble-free gassing was achieved. This value exceeds the required value by 18.5 mg $O_2/(l \cdot h)$. In order to reduce the oxygen transfer rate to the requirement of 19.5 mg $O_2/(l \cdot h)$ a simple reduction in the circular oscillating frequency was made.

Control of the oxygen supply as necessary can also be achieved by altering the concentration of gas in the inflowing gas. In the afore-described apparatus, for example a controlled reference value of 10% air saturation was maintained in such a manner that a continuous air flow of 1 Nl/h was conveyed through the membrane, with which, if necessary, pure oxygen was admixed. The admixing was carried out by means of a magentic valve controlled by a two-position controller, and the actual value of the air saturation in the medium was measured with an oxygen electrode.

The adjustment of the pH value by way of a buffer-$CO_2$ balance, which is customary in cell culture technology, can be achieved by admixing the required amount of $CO_2$ with the inflowing gas.

The process according to the invention and the apparatus according to the invention are suitable, also in advantageous manner, for the bubble-free gassing of microcarrier cultures.

I claim:

1. A process for bubble-free gasification of a liquid culture media for propagating tissue cells, by a gas exchange across an immersed surface of a gas-exchange membrane, which comprises;
   suspending flexibly in the culture media a hollow cylindrical membrane basket formed by hollow, open pore, membrane filaments, the pores being unfilled with the media; and imparting to the membrane basket a pendulum motion without auto-rotation.

2. A process of claim 1, wherein the gassing rate is controlled by altering the angular oscillating frequency or the radius of the pendulum path.

3. A process according to claim 1, wherein the basket is moved by magnetic means.

4. A process for bubble-free gasification of a liquid culture media for propagating tissue cells, by a gas exchange across an immersed surface of a gas-exchange membrane, which comprises;
   suspending flexible in the culture media, a hollow cylindrical membrane basket formed by hollow, open pore, membrane filaments, the pores being unfilled with the media; and imparting a translational motion to the basket; and
   where the gassing rate is controlled by altering the gas concentration or pressure of the gas flowing into the basket.

5. A process for bubble-free gasification of a liquid culture media for propagating tissue cells, by a gas exchange across an immersed surface of a gas-exchange membrane, which comprises;
   suspending flexibly in the culture media, a hollow cylindrical membrane basket formed by hollow, open pore, membrane filaments, the pores being unfilled with the media; and imparting a translational motion to the basket, and wherein the flexible suspension of the membrane cage is effected by means of resilient tubes for the supply and removal of gas.

6. A process for bubble-free gasification of a liquid culture media for propagating tissue cells, by a gas exchange across an immersed surface of a gas-exchange membrane, which comprises;
   suspending flexibly in the culture media, a hollow cylindrical membrane basket formed by hollow, open pore, membrane filaments, the pores being unfilled with the media; and imparting a translational motion to the basket, and
   wherein the basket is suspended by way of an articulated member.

7. A process according to claim 6, wherein the membrane cage is moved by means of an eccentric.

8. Apparatus for bubble-free gasification of a liquid culture media for propagating tissue cells, which comprises;
   a hollow cylindrical membrane basket formed by at least one hollow, open pore, membrane filament adapted to be suspended flexibly in a liquid culture media;
   said pores being resistant to filling with the media when the basket is suspended in the media;
   means for flexibly suspending the basket in a culture media;
   means for introducing a gas into the pores of the membrane filaments; and
   means for imparting a translational motion to the suspended basket; and
   wherein the basket is suspended by way of articulated members.

9. Apparatus according to claim 8, wherein the basket can be moved in a circular or oscillating movement of a pendulum.

10. Apparatus according to claim 8 which further comprises;
    a means for controlling the gassing rate by altering the angular oscillating frequency and the radius of the translational motion.

11. Apparatus according to claim 8 which further comprises;
    a means for altering the gassing rate by controlling the gas concentration and the pressure of the gas flowing into the basket.

12. Apparatus according to claim 8, wherein the basket is suspended by resilient tubes for the supply and removal of gas.

13. Apparatus according to claim 12, wherein the basket has a magnetic core, to which the circular oscillating movement can be imparted by a magnet arrangement provided outside the medium to be gassed.

14. Apparatus according to claim 8, wherein the basket can be moved with the aid of an eccentric, which engages in a guide plate secured to the basket.

15. Apparatus according to claim 14, wherein the axis of symmetry of the guide plate coincides with that of the basket, and that the guide plate is fastened by means of a tension ring support to at least one slotted tension ring that, with the hollow membrane filament or filaments, forms the basket.

* * * * *